(12) United States Patent
Matsuzawa

(10) Patent No.: US 7,191,655 B2
(45) Date of Patent: Mar. 20, 2007

(54) MATERIAL DETERMINATION SYSTEM AND METHOD

(75) Inventor: Kinya Matsuzawa, Shiojiri (JP)

(73) Assignee: Seiko Epson Corporation (JP)

( * ) Notice: Subject to any disclaimer, the term of this patent is extended or adjusted under 35 U.S.C. 154(b) by 191 days.

(21) Appl. No.: 10/916,210

(22) Filed: Aug. 11, 2004

(65) Prior Publication Data

US 2005/0081634 A1 Apr. 21, 2005

(30) Foreign Application Priority Data

Jul. 3, 2003 (JP) ............................ 2003-191158

(51) Int. Cl.
*G01N 29/18* (2006.01)
(52) U.S. Cl. ............................ 73/579; 73/159; 73/597
(58) Field of Classification Search .................. 73/659, 73/658, 646–648, 579, 628
See application file for complete search history.

(56) References Cited

U.S. PATENT DOCUMENTS

| | | | |
|---|---|---|---|
| 3,948,345 A * | 4/1976 | Rosencwaig | ................ 73/579 |
| 5,559,292 A * | 9/1996 | Hull et al. | ..................... 73/597 |
| 5,672,828 A * | 9/1997 | Allan | ............................ 73/579 |
| 5,739,432 A * | 4/1998 | Sinha | ............................ 73/579 |
| 5,767,407 A * | 6/1998 | Sinha | ............................ 73/579 |
| 5,922,960 A * | 7/1999 | Toda | ............................. 73/597 |
| 2003/0025512 A1* | 2/2003 | Wunderer | ................... 324/639 |
| 2004/0187579 A1* | 9/2004 | Yabuta et al. | ................. 73/579 |

FOREIGN PATENT DOCUMENTS

| JP | 2001-337575 | 12/2001 |
|---|---|---|
| JP | 2003-084507 | 3/2003 |

OTHER PUBLICATIONS

Yuusuke Moritake and Hiroomi Hikawa, "Hardware Material Recognition System Using Combinatorial Logic Circuit and Ultrasonic Sensor", Department of Computer Science and Intelligent Systems, Oita University, vol. J85-A, No. 5, May 2002, pp. 610-614.

* cited by examiner

*Primary Examiner*—Hezron Williams
*Assistant Examiner*—Rose M. Miller
(74) *Attorney, Agent, or Firm*—Harness, Dickey & Pierce, P.L.C.

(57) ABSTRACT

A structure including an ultrasonic transducer, a material database, and a material determination section. The ultrasonic transducer transmits ultrasound signals of a plurality of frequencies toward a printing paper over a frequency band covering 40 kHz to 100 kHz or more, and receives reflection signals. The material database stores information representing a reception signal on a material basis. The material determination section makes a material determination for the printing paper based on the information stored in the material database, and the signal (signal derived by amplifying a signal) received by the ultrasonic transducer.

2 Claims, 2 Drawing Sheets

MATERIAL DETERMINATION SYSTEM AND METHOD

FIELD OF THE INVENTION

The present invention relates to a determination system and method suitable for a printer to automatically define a printing paper by its material.

DESCRIPTION OF THE RELATED ART

An ultrasonic transducer is conventionally used for thickness and distance measurement, and material determination. Such an ultrasonic transducer transmits and receives ultrasonic signals, and includes an ultrasonic sensor.

Conventionally, such an ultrasonic transducer used for thickness and distance measurement, and material determination, is often a resonant type that uses piezoelectric ceramics. A resonant type ultrasonic transducer has transmission or reception properties serving well with a specific resonance frequency that is constructively determined.

A material determination system including an ultrasonic transducer generally uses a factor to determine what kind of material an object is made of. The factor is a difference observed in an ultrasonic signal in terms of its absorption and reflection properties. More specifically, an ultrasonic signal is transmitted toward an object, and then the reflected ultrasonic signal is received. Based on any difference found in the reception signal, a material difference is determined as observed.

The resonant type ultrasonic transducer has been conventionally popular, and thus ultrasonic signals have been confined within a narrow frequency band for use. With such a relatively narrow frequency band, however, a difference that is supposed to be found in a reception signal due to any material difference may not always be clearly detected.

To detect such a minute difference, the conventional system often complicates the determination method, or requires an ultrasonic transducer to have a highly-precise property. That is, the conventional system allows detection of any obvious material difference between, for example, iron and fabric, but not any minute difference such as paper quality. Such an ultrasonic transducer may also require special tuning to derive a constant resonance frequency.

For a printer, various types of printing paper are available for any required printing quality, depending on what is to be printed (e.g., paper for photos, or letters and characters). Such printing paper includes plain bond paper, recycled paper, calendered paper, and others. Due to such different materials, there is a demand for automatic detection of the type of paper to prevent erroneous paper selection.

There may also be a case where one would like to use one-side-printable paper, or a case of using one-side-printed paper for printing on blank sides for the sake of manual duplex printing, paper economy, and the like. In such a case, there is a demand for detecting whether the printing side of a sheet has already been printed on or not. Here, the property varies between the printed side of a sheet and the blank side thereof. In this application, such a property difference in terms of the printing side (i.e., whether the side is printed or not (hereinafter, referred to as printing status)), is interpreted as a material difference.

To achieve a detailed material determination including paper quality, printing status, and other situations, use of a material determination system with a conventional ultrasonic transducer will be intricate in structure and require adjustment for a proper reception signal determination.

The present invention has been developed in consideration of the above circumstances, and an object thereof is to provide a material determination system of a simple structure capable of making a detailed material determination for an object.

SUMMARY OF THE INVENTION

To achieve the above object, an aspect of the present invention is directed to a material determination system that includes an ultrasonic signal transmission/reception section for transmitting ultrasonic signals of various frequencies over a predetermined frequency band toward an object, and receiving the reflected signals. A material database for storing information that represents a reception signal on a material basis, and a material determination section for defining the object by its material based on the information stored in the material database and the signals received by the ultrasonic signal transmission/reception section is also provided. With such a structure, the frequency band of the ultrasonic signal is expanded for detection, and any conspicuous differences that are supposed to be found in a reception signal if there is any material difference can be determined. Accordingly, the system structure can be simplified for a material determination.

Another aspect of the present invention is directed to a material determination system that includes an ultrasonic signal transmission/reception section for transmitting ultrasonic signals of various frequencies over a predetermined frequency band toward a decision object, and receiving the reflected signals. A specific information storage section for storing information that represents a reception signal corresponding to the object made of a specific material, and a material determination section for defining the object by its material based on the information stored in the specific information storage section and the signals received by the ultrasonic signal transmission/reception section are also provided. With such a structure, the frequency band of the ultrasonic signal is expanded for detection, and any conspicuous differences that are supposed to be found in a reception signal if specific material difference is observed for an object based on the printing stats, and others can be determined. Accordingly, the system structure can be simplified for a material determination.

In still another aspect of the present invention, the ultrasonic signal transmission/reception section transmits ultrasonic signals of various frequencies over a predetermined frequency band toward the object at a plurality of given points scattered across a range that covers at least half or more of the object's surface area. Such a structure allows material determination with high precision by using a wider surface area of the object for detection.

In still another aspect of the present invention, the ultrasonic signal transmission/reception section transmits ultrasonic signals of various frequencies over a predetermined frequency band toward the object at all or each of a plurality of given points scattered within a range that covers, at the most, less than half of the object's surface area. Such a structure allows for material determination in a short amount of time by confining the surface area of the object for detection.

In still another aspect of the present invention, a determination result notification section is further provided for notification of a material determination result of the object based on a determination result derived by the material determination section. With such a structure, in a case, for example, where the object is printing paper for use in a printer located away over a network, the determination result can be available at a location some distance from the object.

Still another aspect of the present invention is directed to a material determination method that includes an ultrasonic signal transmission/reception step of transmitting ultrasonic signals of various frequencies over a predetermined frequency band toward the object, and receiving the reflected signals. The method also includes a material determination step of defining, using a material database that stores information that represents a reception signal on a material basis, the object by its material based on the information in the material database, and based on the signals received by the ultrasonic signal transmission/reception step.

Still another aspect of the present invention is directed to a material determination method that includes an ultrasonic signal transmission/reception step of transmitting ultrasonic signals of various frequencies over a predetermined frequency band toward the object, and receiving the reflected signals. The method also includes a material determination step of defining, using specific information storage means that store information that represents a reception signal that corresponds to the object made of a specific material, the decision object by material based on the information in the specific information storage means, and based on the signals received by the ultrasonic signal transmission/reception step.

Note here that, in the above aspects of the present invention, the system structure may include an electrostatic ultrasonic transducer having a wide frequency band for transmission and reception of ultrasonic signals. If this is the case, ultrasonic signals with a high sound pressure level across the wide frequency band will be derived. Accordingly, the ultrasonic signal transmission/reception section can be reduced in size or simplified in process for adjustment.

In an alternative structure, a component may be included for measuring the distance to the decision object using a time between transmission and reception as a basis therefor. In such a case, for example, the resulting printer becomes capable of detecting not only the material quality but also the printing paper thickness, or the remaining sheet quantity.

DETAILED DESCRIPTION OF THE PREFERRED EMBODIMENTS

Below, an embodiment of a material determination system according to the present invention is described with reference to the accompanying drawings. In the embodiment, printing paper is presumably an object for a material determination.

Figure 1:
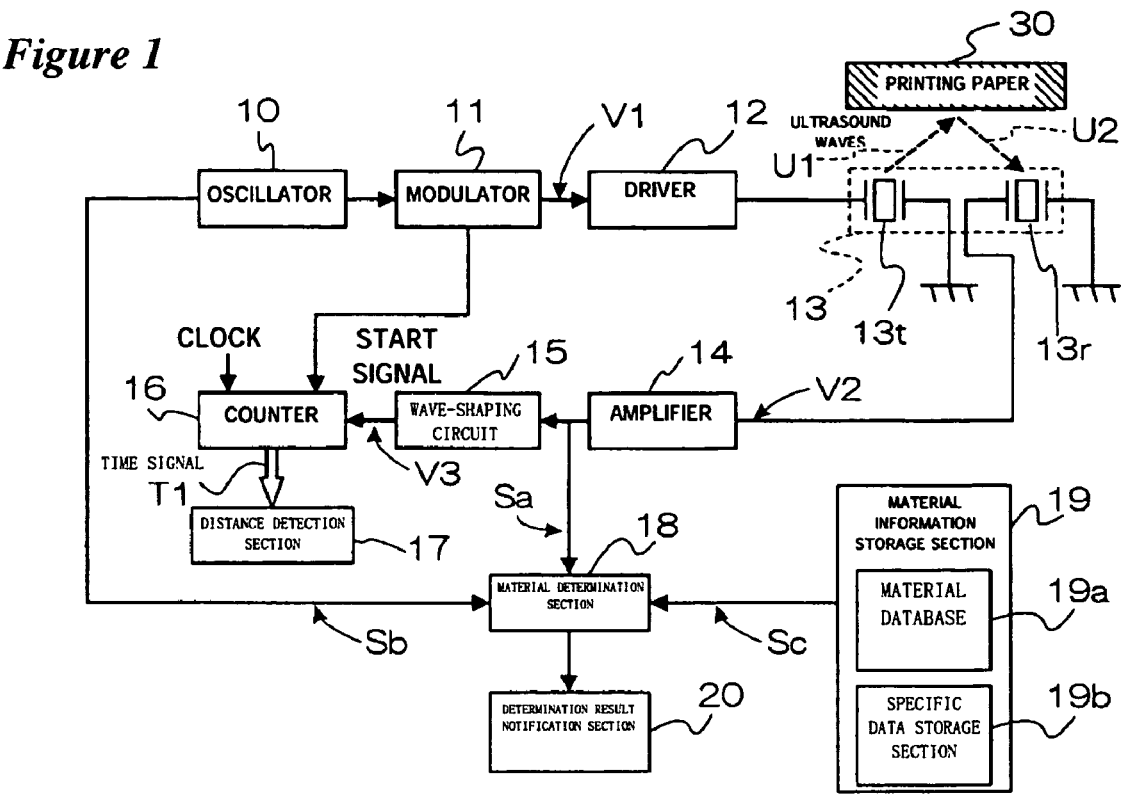
FIG. 1 is a block diagram showing the structure of an embodiment of a material determination system of the present invention.
Figure 2:
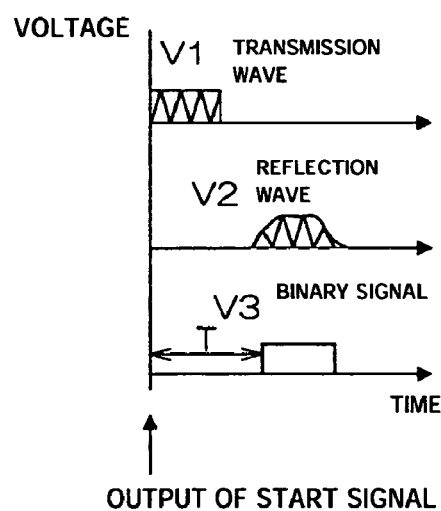
FIG. 2 is an operation waveform diagram of the structure of FIG. 1.

FIG. 1 is a block diagram showing the structure of a material determination system of the present invention, and FIG. 2 is a waveform diagram of a temporal voltage change observed for the respective operating components. In FIG. 1, an oscillator 10 generates an alternating signal while repeatedly varying (sweeping) the frequency in a given time period over a frequency band in the range of 40 kHz to 100 kHz, or more. A modulator 11 repeatedly outputs a rectangular wave signal of a predetermined time frame as a result of a modulation using an output signal from the oscillator 10. The modulator 11 also outputs a start signal that indicates the output start time of the corresponding rectangular wave signal. Refer to FIG. 2 for a waveform V1 of the rectangular wave signals output from the modulator 11. A driver 12 amplifies the output signals from the modulator 11 to a predetermined size, and outputs the results. The output results from the driver 12 are applied to an ultrasonic transducer 13 so that a transmitter 13t in the ultrasonic transducer 13 transmits the ultrasonic signals that have a frequency of 40 kHz or more.

The ultrasonic transducer 13 includes the transmitter 13t for ultrasound transmission, and a receiver 13r for ultrasound reception. The transmitter 13t generates an ultrasound signal U1, which is to be reflected by a printing paper 30 which is an ultrasound exposure object. The thus reflected ultrasonic signal (i.e., the ultrasonic signal U2) is received by the receiver 13r. The transmitter 13t and the receiver 13r structure the electrostatic ultrasonic transducer (ultrasonic sensor) to have a wide frequency band.

An output V2 of the receiver 13r is amplified by the amplifier 14, and then shaped by a wave-shaping circuit 15. The resulting signal is a binary signal V3 as shown in FIG. 2. A counter 16 uses a predetermined clock signal as a reference to measure an elapsed time T between inputs of a start signal and a binary signal V3. The measurement result is output as a time signal T1, which has a value that corresponds to the distance to the printing paper 30 (i.e., length of an ultrasound reflection path). The time signal T1 thus measured in the counter 16 is forwarded to a distance detection section 17.

The distance detection section 17 includes a CPU (Central Processing Unit), and semiconductor memory exemplified by a RAM, a ROM, or some other type of memory. Through execution of a program stored in such a memory, the thickness of the printing paper 30 and the remaining sheet quantity in a paper feed tray in accordance with the time signal T1 may be detected. The detection results are then output. Here, for detection of the paper thickness, the ultrasonic transducer 30 may be placed at a position where a sheet of paper passes by (e.g., at the midpoint of a feeding mechanism in the printer). For detection of the remaining sheet quantity, the ultrasonic transducer 30 may be placed at a position where the paper in the paper feed tray is exposed to ultrasound waves, for example. Herein, the ultrasonic transducer 30 may be provided singularly or plurally.

Similarly to the distance detection section 17, the material determination section 18 includes a CPU, semiconductor memory exemplified by a RAM, a ROM, or some other type of memory, and additionally an A/D converter (analog/digital converter) for receiving an output Sa from the amplifier 14, and the like. Through execution of a program stored in such a memory, the printing paper 30 is defined by its material in accordance with the reception signal Sa provided by the amplifier 14. In an alternative structure, the material determination section 18 may be structured to be a piece with the distance detection section 17 and the determination result notification section 20 (i.e., structured to share the CPU or other components). In addition to the reception signal Sa coming from the amplifier 14, the material determination section 18 receives a signal Sb coming from the oscillator 10 to indicate the oscillation frequency, and data Sc stored in the material information storage section 19 for every material. The material determination section 18 stores the reception signal Sa based on the signal Sb, which corresponds to the frequencies of a plurality of given points scattered across the frequency band covering the range of 40 kHz to 100 kHz, or more. At such a plurality of frequency points, the reception signal Sa and the respective data Sc are compared, and the comparison result is used for a material determination of the printing paper 30.

The material information storage section 19 includes a memory such as a ROM or any other type of memory, and is structured by a material database 19a and a specific data storage section 19b. The material database 19a stores the frequency characteristics of the reception signal on a material basis. The specific data storage section 19b stores the frequency characteristics of the reception signal of a case where a determination side (i.e., the side on which the ultrasonic signal is reflected) of the printing paper 30 is already printed. The frequency characteristics of the reception signal is stored plurally if storage is made on a material basis, and stored singularly if storage is made for every material as a whole.

The determination result notification section 20 outputs, in a predetermined format, the material determination result derived by the material determination section 18 for the printing paper 30. Alternatively, the determination result notification section 20 may be so structured as to merely output the determination result to a printing mechanism (printing engine section) that is not shown. In an alternative structure, the determination result notification section 20 may receive information about the paper material (e.g., calendared paper or plain paper) designated by the printing mechanism, and if the designated paper material is not in agreement with the determination result, make a notification using a display or a beep generator (neither is shown). Still alternatively, if the printing side is already printed, the determination result notification section 20 may output the information onto a computer screen connected over a network or a printer cable (neither is shown) from which a printing command comes. Still alternatively, the determination result notification section 20 may be provided with the capability of outputting information about the paper thickness and the remaining sheet quantity detected by the distance detection section 17.

Figure 3:
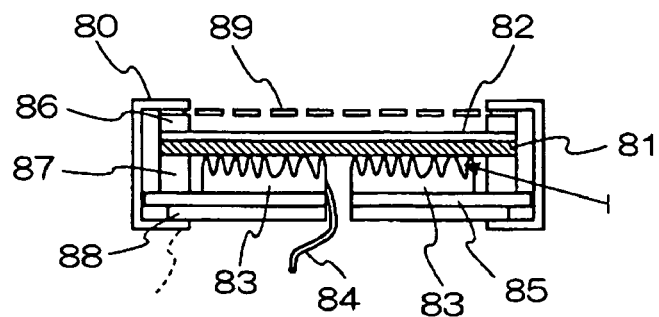
FIG. 3 is a schematic cross section showing the structure of an ultrasonic transducer 13 of FIG. 1.
Figure 4:
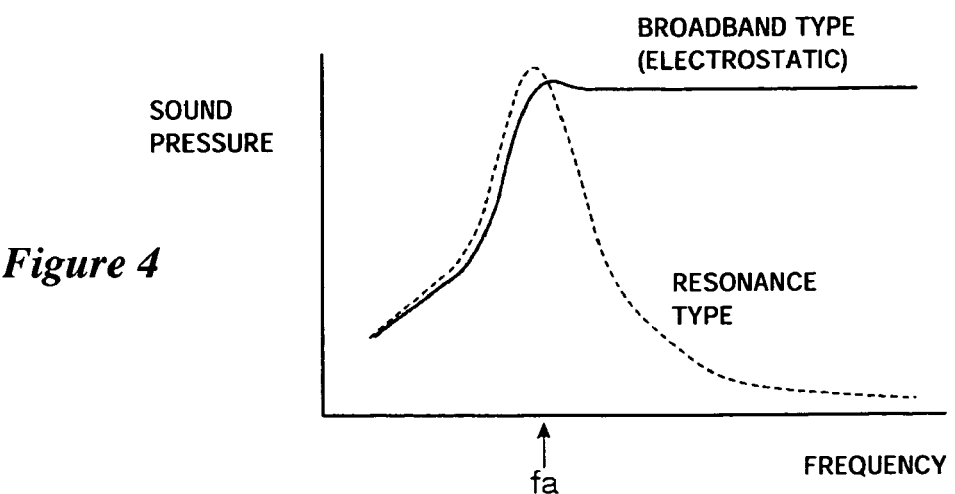
FIG. 4 is a diagram showing the frequency characteristics of an ultrasonic transducer of FIG. 3.

Described next is an exemplary structure of the ultrasonic transducer 13 of FIG. 1 by referring to FIGS. 3 and 4. The ultrasonic transducer of FIG. 3 is an electrostatic ultrasonic transducer. Such an electrostatic ultrasonic transducer (ultrasonic sensor) as shown in FIG. 3 oscillates by electrostatic effects has broadband frequency characteristics (FIG. 4). Referring to FIG. 4, a frequency fa is about 40 kHz, and the sound pressure level for the frequency is 100 dB or more under any given requirements. In FIG. 4, for comparison, the property of a resonant type ultrasonic transducer is indicated by dashed lines.

The electrostatic ultrasonic transducer of FIG. 3 has an oscillator of a derivative 81 (insulator) such as PET (polyethylene terephthalate) of a few μm (about 3 to 10 μm) thickness. Onto the upper surface of the derivative 81, an upper electrode 82 formed as a metal leaf is evaporated to be a piece therewith, for example. On the lower surface of the derivative 81, a lower brass electrode 83 is placed so as to abut thereto. The derivative 81 forms an oscillation film. The lower electrode 83 is connected with a lead 84, and is fixed to a base plate 85 made of Bakelite or other material. The derivative 81, the upper electrode 82, and the base plate 85 are all crimped together by a case 80 with metal rings 86, 87, and 88, and mesh 89.

On the side of the derivative 81 of the lower electrode 83, a plurality of minute recesses (about a few tens and a few hundreds of μm) varying in shape are formed. These minute recesses form cavities between the lower electrode 83 and the derivative 81, and accordingly the capacitance distribution slightly changes between the upper and lower electrodes 82 and 83. Such shape-varying minute recesses are formed by manually filing the surface of the lower electrode 83. As such, an electrostatic ultrasonic transducer can have broadband frequency characteristics through formation of countless capacitors varying in cavity size and depth.

In a case where the ultrasonic transducer 13 of FIG. 1 is an electrostatic ultrasonic transducer of FIG. 3, the sensor drive voltage will be an alternating voltage of about 50 to 150V at its peak. The bias voltage for absorption of the upper electrode 82 is about DC 50 to 150V. Herein, the lower electrode 83 is not necessarily formed with a plurality of minute recesses as shown, and may be mirror-finished.

Figure 5:
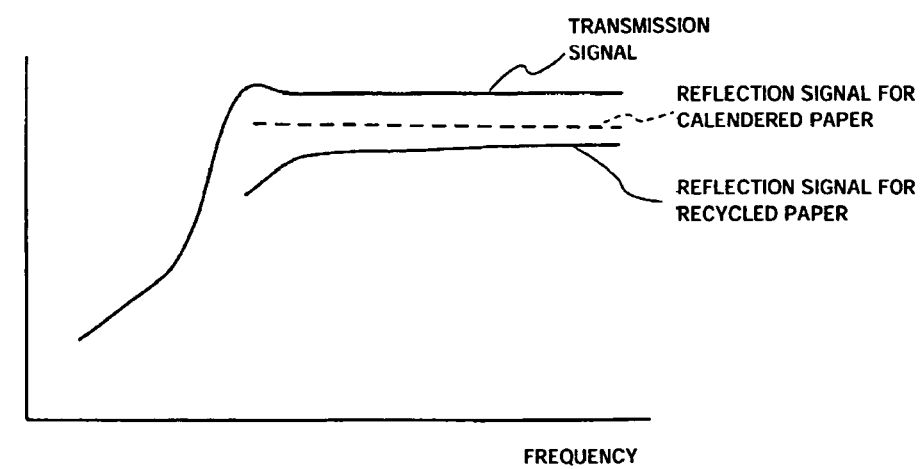
FIG. 5 is a diagram showing the frequency characteristics of transmission signals from an ultrasonic transducer of FIG. 4 and reception signals in terms of material.

Referring to FIG. 5, described next is data to be recorded to the material database 19a of FIG. 1. FIG. 5 is a plot diagram of, with the broadband ultrasonic transducer of FIG. 3, transmission signals (oscillation signals) coming from the transmitter 13t, and reception signals in terms of paper quality. The plot data is not derived merely by a certain frequency, but by plotting reflection signals at the time of frequency sweeping over a band in which the oscillation signals of the ultrasonic transducer show the flat characteristics.

A coarse but soft paper such as recycled paper absorbs energy in the low-frequency region, thereby reducing the level of the reflection signals. With a frequency increase, however, the rate of decrease is lowered. On the other hand, when paper having a relatively hard surface such as calendered paper is used, signals having a high reflected sound pressure can be observed across a wide frequency band.

Based on the observation values of FIG. 5, the material database 19a of FIG. 1 is structured so as to plurally store a reception signal level at a plurality of predetermined frequencies on a material basis. Such data is empirically collectable through incorporation of the present system into a printer.

When one-side-printable paper is erroneously set on a paper feed tray, for example, with confusion between the already-printed-side and the blank side, additionally with frequency sweeping, area scanning is performed after the ultrasonic transducer 13 is moved in position. The reception signal level shows a change between the printed position and not-printed position. This change may vary depending on the material and the frequency, and thus the waveform is to be stored for every material and frequency every time any level change is observed to the reception signal. The data storage is done with respect to the specific data storage section 19b after a predetermined process of normalization and others is executed for every material and frequency. Based on the data thus stored in the specific data storage section 19b, the reception signal Sa, and information coming from a movement mechanism (not shown) about the position of the ultrasonic transducer 13 after it has moved, the material determination section 18 determines whether the determination side of the printing paper 30 has been already printed on. In this manner, by referring to the determination result derived by the material determination section 18, the determination result notification section 20 can notify a user that the paper setting is wrong.

The issue here is that raw reflection signals always have the lower sound pressure than transmission (oscillation) signals due to attenuation in the air. However, when the paper (e.g., printer paper) and the sensor are positioned closely together, such a thing does not cause a problem.

As described in the foregoing, according to the present embodiment, a material determination can be made for printing paper (printing status included) by scanning the surface thereof in a printer using an ultrasonic transducer. That is, an object exemplified by printing paper and others can be defined by material utilizing the present system and ultrasonic signals.

Note that, in the above embodiment, the ultrasonic transducer 13 is moved against the printing paper 30. This is not restrictive, and the ultrasonic transducer 13 may be fixed at the midpoint exemplarily of a paper feed mechanism. With such a structure, the printing paper 30 may be moved in position, or both the printing paper 30 and the ultrasonic transducer 13 may be moved in position.

Alternatively, through movement of the ultrasonic transducer 13 and the printing paper 30, ultrasonic signals may be transmitted of various frequencies over a predetermined frequency band at a plurality of given points scattered across a range covering at least half or more of a surface area of the printing paper 30. Still alternatively, ultrasonic signals may be transmitted of various frequencies over a predetermined frequency band at all or each of a plurality of given points scattered within a range covering at the most less than half of the surface area of the printing paper 30. The former case favorably leads to the more precise decision making, and the latter case leads to the faster decision making.

In the structure of FIG. 1, the ultrasonic transducer 13, or the components covering the oscillator 10 to the amplifier 14 including the ultrasonic transducer 13 correspond to ultrasonic signal transmission/reception means for transmitting ultrasonic signals of various frequencies over a predetermined frequency band toward an object, and receiving the reflected signals. In the material information storage section 19, the material database 19a corresponds to a material database storing information representing a reception signal on a material basis, and the specific information storage section 19b corresponds to specific information storage means for storing information that represents a reception signal corresponding to the specific material of the object. The material determination section 18 corresponds to material determination means defining the object by material based on the information stored in the material database, or the information stored in the specific information storage means and the signal received by the ultrasonic signal transmission/reception means.

The object in the present system is not restricted to the printing paper as above, and may be a thing as long as it causes a difference of surface material in a reflection signal as a result of ultrasound wave exposure.

What is claimed is:

1. A material determination system, comprising:
    an oscillator adapted to generate an alternating signal while repeatedly varying a freguency over a freguency band in the range of 40 kHz to 100 kHz;
    a modulator adapted to output a rectangular wave signal using an output signal from said oscillator;
    a driver adapted to amplify the output signal from said modulator and output an amplified signal;
    an ultrasonic transducer including a transmitter and a receiver, said transmitter adapted to transmit the amplified signal over a predetermined frequency band toward a plurality of sheets of paper, and said receiver for adapted to receive reflected signals from said plurality of sheets of paper;
    an amplifier that amplifies an output signal from said receiver;
    a wave-shaping circuit that shapes said amplified output signal into a binary signal;
    a counter that measures an elapsed time between a start signal and said binary signal, said elapsed time corresponding to a distance to said plurality of sheets of paper;
    a distance detection section adapted to receive said elapsed time from said counter, said distance detection section adapted to detect a quantity of said sheets of paper based on said elapsed time;
    a material database for storing information that represents a reception signal on a material basis; and
    material determination device for defining a type of paper by its material based on the information stored in the material database and the signals received by the ultrasonic transducer.

2. The material determination system according to claim 1, further comprising:
    determination result notification device for making a notification of a material determination result about the paper based on the determination result derived by the material determination device.

\* \* \* \* \*